(12) United States Patent
Watkins, Jr.

(10) Patent No.: US 8,829,929 B1
(45) Date of Patent: *Sep. 9, 2014

(54) METHOD AND APPARATUS FOR MEASURING DEGRADATION OF RUBBER PRODUCTS

(76) Inventor: Kenneth S. Watkins, Jr., Dahlonega, GA (US)

( * ) Notice: Subject to any disclaimer, the term of this patent is extended or adjusted under 35 U.S.C. 154(b) by 511 days.

This patent is subject to a terminal disclaimer.

(21) Appl. No.: 12/214,911

(22) Filed: Jun. 24, 2008

Related U.S. Application Data

(63) Continuation-in-part of application No. 10/506,518, filed as application No. PCT/US03/06844 on Mar. 5, 2003, now Pat. No. 7,414,416.

(60) Provisional application No. 60/362,157, filed on Mar. 6, 2002.

(51) Int. Cl.
| | |
|---|---|
| *G01N 17/00* | (2006.01) |
| *G01N 27/04* | (2006.01) |
| *G01N 33/44* | (2006.01) |
| *C08J 5/12* | (2006.01) |

(52) U.S. Cl.
USPC .......................... 324/693; 73/866; 428/539.5

(58) Field of Classification Search
USPC ......... 73/86–87, 865.6, 865.9–866; 324/71.1, 324/541, 543, 555, 691, 693; 374/57; 422/53; 252/506; 428/539.5
See application file for complete search history.

(56) References Cited

U.S. PATENT DOCUMENTS

| | | | |
|---|---|---|---|
| 3,603,142 A | 9/1971 | Saylak | |
| 5,378,991 A * | 1/1995 | Anderson et al. | 324/557 |
| 6,291,568 B1 | 9/2001 | Lussey | |
| 6,495,069 B1 | 12/2002 | Lussey et al. | |
| 6,646,540 B1 | 11/2003 | Lussey | |
| 7,612,325 B1 * | 11/2009 | Watkins et al. | 250/222.2 |
| 8,217,669 B1 * | 7/2012 | Watkins, Jr. | 324/693 |
| 2007/0166831 A1 * | 7/2007 | Watkins et al. | 436/149 |

* cited by examiner

*Primary Examiner* — Thomas P Noland
(74) *Attorney, Agent, or Firm* — Gronholm Patent Services, LLC

(57) ABSTRACT

An environmental degradation sensor for rubber products comprises a conductive composite having a matrix of at least one polymeric component of the rubber product, a conductive filler, and a degradation control agent. The sensor is attached to the rubber product and communicates with a reader through electrical contact or by use of a radio frequency identification device.

20 Claims, 13 Drawing Sheets

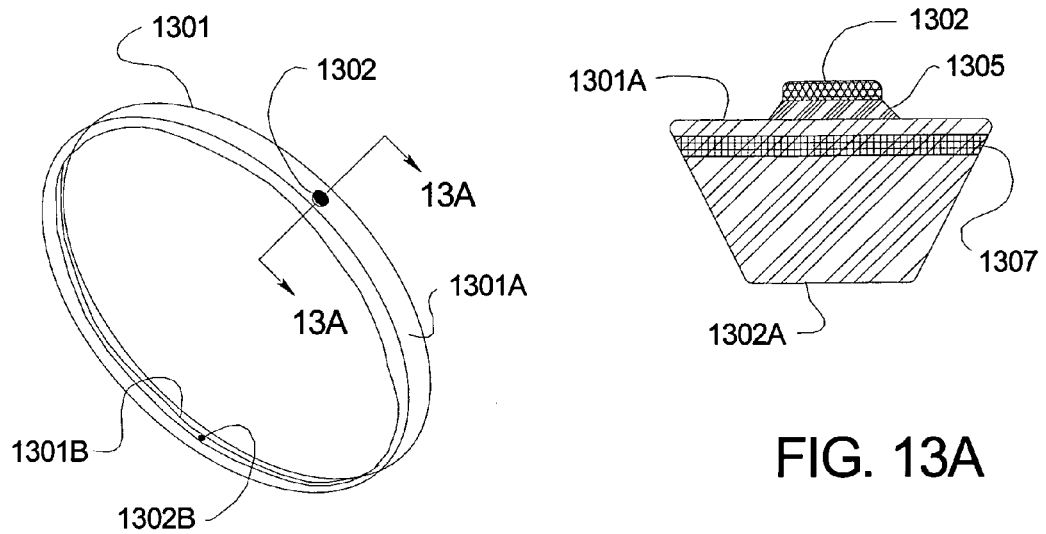
FIG. 13
FIG. 13A
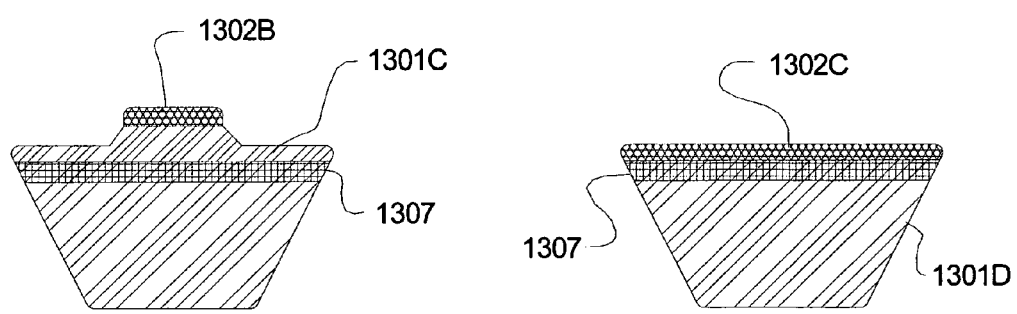
FIG. 13B
FIG. 13C

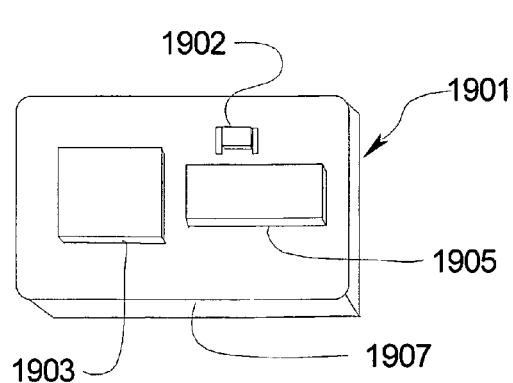
FIG. 19
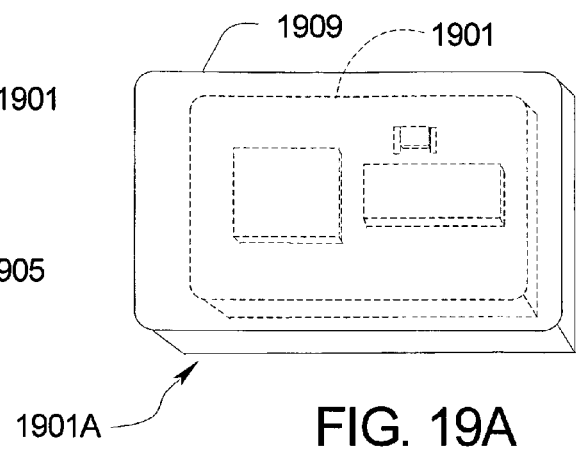
FIG. 19A
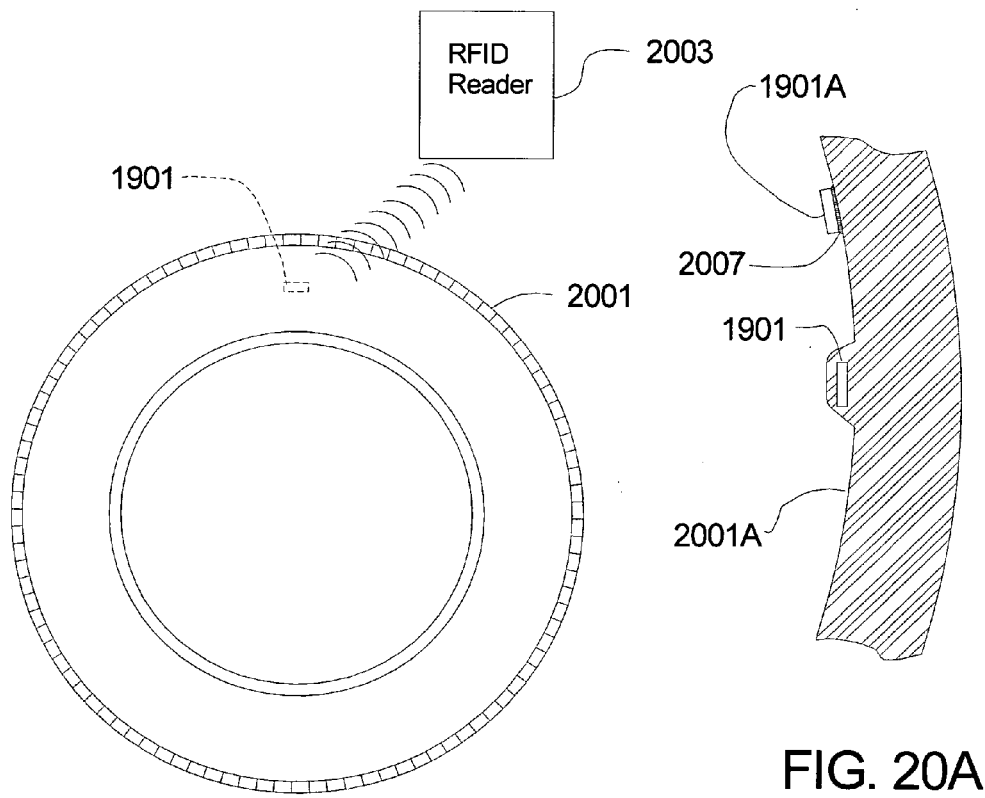
FIG. 20
FIG. 20A

METHOD AND APPARATUS FOR MEASURING DEGRADATION OF RUBBER PRODUCTS

This application is a Continuation-in-Part Application of U.S. application Ser. No. 10/506,518, filed May 9, 2005 currently issued as U.S. Pat. No. 7,414,416, which claims the benefit of a prior filing date of PCT Application PCT/US03/06844 filed Mar. 5, 2003 which claims the benefit of a prior U.S. Provisional Application No. 60/362,157 filed Mar. 6, 2002 and further claims the benefit of U.S. application Ser. No. 11/552,197, filed Oct. 24, 2006, currently abandoned, which claims benefit of prior U.S. Provisional Application No. 60/729,579 filed Oct. 24, 2005.

FIELD OF THE INVENTION

The present invention relates to polymeric products with integral degradation sensors, and more particularly, molded and extruded industrial rubber products with conductive composite degradation sensors.

BACKGROUND OF THE INVENTION

A great many products used by consumers, businesses and organizations degrade unacceptably unless stored in controlled environments. These products include industrial rubber products such as tires, rubber hoses, belts, engine mounts, seals, gaskets and other products. Although quantitative methods are available to measure mechanical or chemical degradation of these products, these methods are often difficult to use, require expensive equipment and training, and are rarely used in consumer products.

Visual and tactile inspections of these items is the method most commonly used for consumer and many commercial and industrial rubber products. Visual inspections are often difficult because degraded products may not be fully visible. Tactile inspections, such as squeezing a hose is very subjective and is not satisfactory in many applications.

An improved method is needed to monitor the condition of consumer and commercial/industrial rubber products that overcomes the drawbacks of current methods.

OBJECTS AND SUMMARY OF THE INVENTION

Therefore, an object of the present invention is to provide an environmental degradation sensor and method for monitoring the condition of molded and extruded rubber products.

Another object of the present invention is to provide a degradation sensor for rubber products which may be attached to an outside surface of the product and read by a simple, low cost contact reader.

Still another object of the present invention is to provide a degradation sensor which detects high cycle fatigue before failure of the product.

Yet another object of the present invention is to provide a smart RFID label or tag for rubber products which provide complete product identification and product condition.

For the purposes of this disclosure, polymeric articles with integral degradation sensors include any articles comprising polymeric component(s) with conductive composite degradation sensors embedded or attached to the article. The polymeric component(s) of the article may include thermoplastics and thermosets and made by various molding, extrusion, dipping, spraying or other processes. Such articles include consumer, commercial and industrial rubber and automotive products including tires, hoses, belts, seals, gaskets and isolation mounts made of natural rubber, synthetic rubber, or other elastomers. Such articles also include structures comprising protective coatings, structures made of engineered plastics and composites.

An environmental degradation sensor for rubber products comprises a conductive composite having a matrix of at least one polymeric component of the rubber product, a conductive filler, and a degradation control agent. The sensor is attached to the rubber product and communicates with a reader through electrical contact or by use of a radio frequency identification device.

The sensor may be manufactured separately and attached to the rubber product by bonding, adhesives, molding with the product, or mechanical fasteners. Or, the sensor may be co-molded or co-extruded during manufacture of the product.

In another embodiment, the sensor is formed separate from the rubber product and attached electrically to a passive radio frequency identification device. The device may be embedded in the rubber product, or it may be attached to an inside surface of the product by adhesives, bonding or mechanical fasteners.

A reader for a contact sensor may be a simple resistance measuring device like an ohmmeter calibrated for remaining life or percentage of life used. Or, the reader may be a threshold reader responding to a preselected threshold of resistance indicating a unsatisfactory state of the product.

Correlation of sensor resistance and product degradation is made by accelerated aging of the sensor and the product material and measuring a degradation property such as elongation at break and sensor resistance. Measurement at multiple temperatures allows determination of the activation energy by both property degradation and measurement of sensor resistance. Analysis such as Arrhenius analysis to allow prediction of remaining life.

BRIEF DESCRIPTION OF THE DRAWINGS

These and other features, aspects and advantages of the present invention will become better understood with regard to the following description, appended claims and accompanying drawings where:

FIG. 13 is a perspective drawing of a V drive belt having a contact conductive composite multi function degradation sensor;

FIG. 13A is a cross section of the drive belt of FIG. 13 having a contact sensor attached by a bonding agent;

FIG. 13B is an alternative embodiment of a contact sensor for a drive belt;

FIG. 13C is another embodiment of a contact sensor forming an outside surface of a drive belt;

FIG. 19 is a perspective drawing of a passive RFID tag incorporating a conductive composite degradation sensor;

FIG. 19A is the tag of FIG. 19 encased in an insulative protective cover;

FIG. 20 is a tire showing the passive RFID tag of FIG. 19 attached to an inside wall of the tire;

FIG. 20A is a cross section drawing showing two embodiments for attaching a RFID tag to the sidewall of a tire;

DESCRIPTION OF THE PREFERRED EMBODIMENTS

The following is a description of the preferred embodiments of conductive composite degradation sensors and readers for detecting degradation of rubber products.

Prior work disclosing use of conductive composites to model aging of polymeric materials is disclosed in U.S. application Ser. No. 11/510,875, filed Aug. 23, 2006 and Ser. No. 10/506,518, hereby incorporated by reference. These references show a general decrease in resistivity of a conductive composite made of a polymeric matrix and conductive particle filler as the composite degrades. This is due to various degradation mechanisms such as mass loss, chain cross linking, and chain scission of the polymer matrix, resulting in a higher volume fraction of conductive particles as the polymer degrades.

Figures 1, 1A:
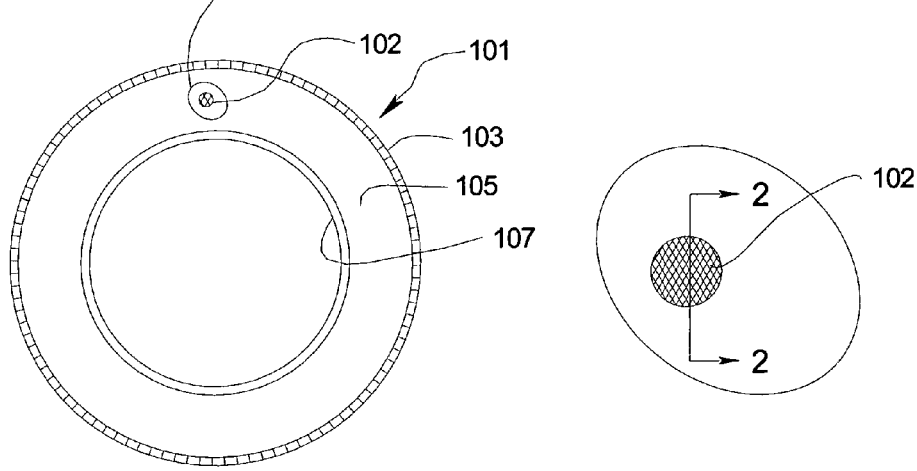
FIG. 1 is a side elevation drawing of a tire having a contact sensor attached to a sidewall.
FIG. 1A is a detail of the contact degradation sensor of FIG. 1.

FIG. 1. is a side elevation drawing of a molded industrial rubber product such as tire 101 having a outer tread 103, product portion or sidewall 105 and inner rim portion 107. Degradation sensor 102 is a conductive composite disposed on an outside surface of the tire, such as on sidewall 105, better shown in FIG. 1A. Tire 101 is shown as a representative product only. Other molded products such as rubber or plastic hose, seals, gaskets, isolation mounts and other molded products and are represented by FIG. 1A, and FIG. 2-FIG. 2B.

Figures 2, 2A, 2B:
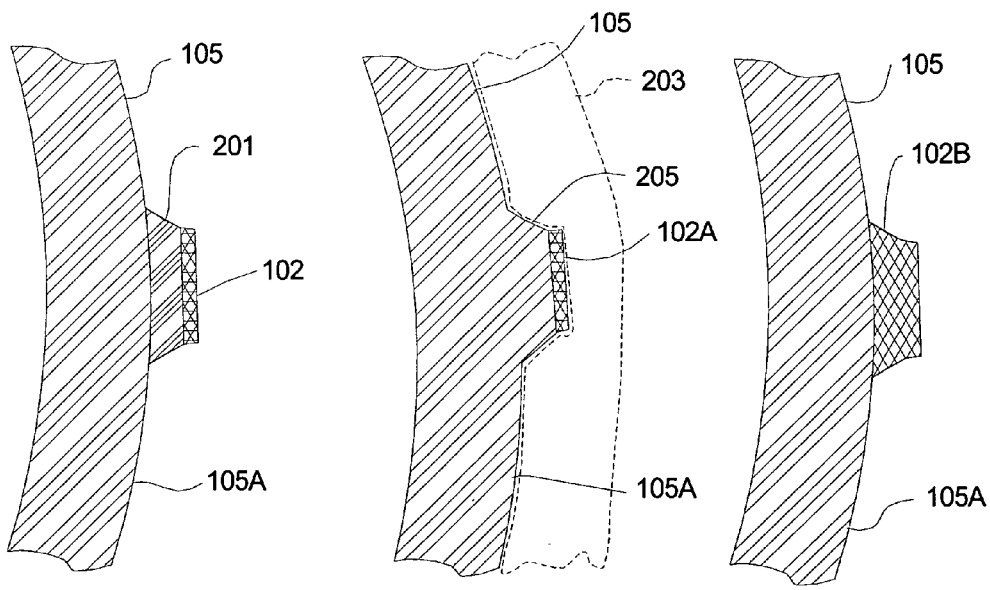
FIG. 2 is a cross section of the contact sensor taken along lines 2-2 of FIG. 1A.
FIG. 2A is an alternative embodiment showing a contact sensor mold bonded to the sidewall of the tire of FIG. 1.
FIG. 2B is an alternative embodiment showing a contact sensor formed as a hot melt on the sidewall of the tire of FIG. 1.

FIG. 2 is a cross section of sensor 102 and a portion of sidewall 105 taken along lines 2-2 of FIG. 1. In the preferred embodiments, sensor 102 is a conductive composite element such as a disc made of a conductive composite compound. In the preferred embodiments, the conductive composite compound utilizes at least one of the polymeric components of tire 101 and a conductive filler. A control agent, such as an antioxidant may be added as discussed later. Sensor element 102 is bonded to sidewall 105 by a bonding agent 201. Bonding agent 201 may be an adhesive, a hot melt compound, an adhesive tape, or other bonding agents known in the art. Adhesives which may be used include solvent based adhesives, polyurethane based adhesives, silicone based adhesives, epoxies, cyanoacrylate adhesives, and other adhesive known in the art.

In the preferred embodiments, sensor 102 may be molded, cast or milled from the conductive composite compound. In the preferred embodiments, sensor 102 is cured or partially cured prior to bonding to tire 101. Sensor 102 may be applied prior to, or after final curing of, tire 101. In other embodiments, sensor 102 is die-cut from a conductive composite film.

FIG. 2A is an alternative embodiment of attaching a sensor 102A to tire 101 by curing tire 101 with a pre-formed sensor disc 102A positioned in mold 203. Sensor 102A bonds directly to product 101 during molding and curing. Mold well 205 serves as a retainer for sensor 201A during the molding process and results in sensor 102A raised above surface 105A. In other embodiments, well 205 is eliminated and sensor 102A is flush with surface 105A, similar to sensor 302 of FIG. 4.

FIG. 2B is another embodiment of attaching degradation sensor 102B to sidewall 105. In the preferred embodiment, sensor 102B is a hot-melt adhesive, made by compounding a polymeric matrix and a conductive filler. In other embodiments, sensor 102B is a conductive adhesive such as a conductive epoxy.

The respective degradation sensors of these embodiments are conductive composites having a matrix of a selected polymer having similar degradation characteristics as at least one of the product polymers, such as one of the polymers utilized in tire 101. In the preferred embodiments, the selected material comprises at least one of the polymeric components of product itself. The conductive filler may be carbon black, a metallic powder, or a metallic oxide. A degradation control agent as discussed later may be added to the sensor. The product, such as tire 101 may be a natural or synthetic rubber material, or it may be a thermoplastic or other thermoset polymer. It may have internal reinforcement.

In the preferred embodiments, the degradation sensors of FIGS. 2-2B are raised above the respective tire surface 105A to provide a tactile means for locating the sensor. In other embodiments, the respective sensors are flush, or depressed below, surface 105A. Although sensor 102 is shown on sidewall 105 of FIG. 1, the sensor may be located on any outside surface portion of the product, such as within the tread grooves, or rim of the tire.

Figure 3:
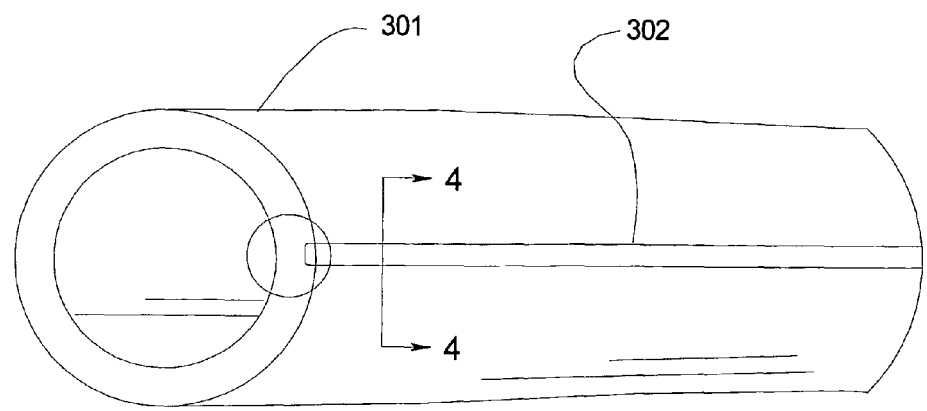
FIG. 3 is a perspective drawing of an extruded rubber hose having an extruded conductive composite sensor strip.

FIG. 3 is a perspective drawing of an extruded rubber product such as extruded hose 301 having an integral degradation sensor 302. Hose 301 is representative only. Other extruded products such as wire and cable insulation and jackets, seals, gaskets, and other extruded products may incorporate the degradation sensors of these embodiments and are represented by FIGS. 4-4B.

Figure 4:
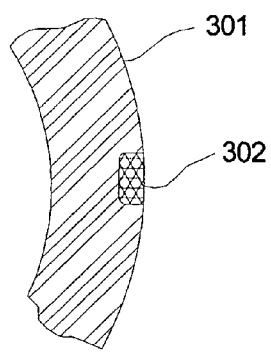
FIG. 4 is a cross section of the sensor strip taken along lines 4-4 of FIG. 3.

FIG. 4 is a cross section of hose 301 taken along lines 4-4 of FIG. 3. In this embodiment, sensor 302 is a conductive composite strip, co-extruded with hose 301. In the preferred embodiments, sensor 302 comprises at least one polymeric component of hose 301 and a conductive filler as discussed later.

Figure 4A:
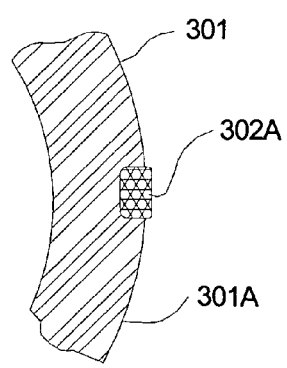
FIG. 4A is an alternative embodiment of an extruded sensor strip having a raised surface.

FIG. 4A is an alternative embodiment of hose 301 of FIG. 3 having a co-extruded sensor 302A extending above surface 301A of hose 301. Extending sensor 302A above surface 301A provides a tactile means for identifying sensor 302A.

Figure 4B:
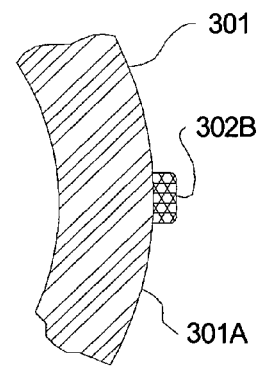
FIG. 4B is another embodiment of an extruded sensor strip.

FIG. 4B is an alternative embodiment of hose 301 of FIG. 3 having sensor 302B deposited on hose surface 301A. Sensor 302B may be a hot melt, or it may be a separately formed conductive composite strip attached to hose 301 by an adhesive.

The respective sensors of FIG. 3 and FIGS. 4-4B are conductive composites having a matrix of a selected polymer having similar degradation characteristics as the product material such as hose 301 material. In the preferred embodiments, the selected polymer comprises at least one of the polymeric components of the product material. The conductive filler may be carbon black, a metallic powder, or a metallic oxide. A degradation control agent as discussed later may be added to the sensors.

Figure 5:
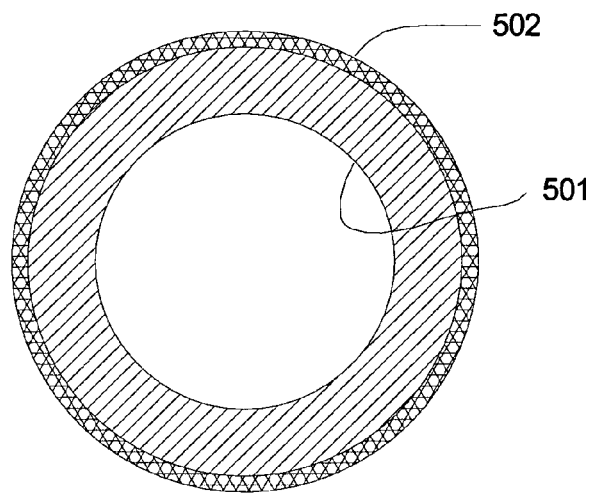
FIG. 5 is a cross section of a rubber hose having an outer layer molded or extruded as a conductive composite degradation sensor.

FIG. 5 is a cross section of a polymeric hose 501 having a molded or extruded outer sensor layer 502. Sensor layer 502 is a conductive composite having a matrix of a selected polymer having similar degradation characteristics as hose 501 material. In the preferred embodiments, the selected material comprises at least one of the polymeric components of hose 501 material. The conductive filler may be carbon black, a metallic powder, or a metallic oxide. A degradation control agent as discussed later may be added to sensor layer 502. Hose 501 may be a natural or synthetic rubber material, or it may be a thermoplastic or other thermoset polymer. It may have internal reinforcement.

Figure 6:
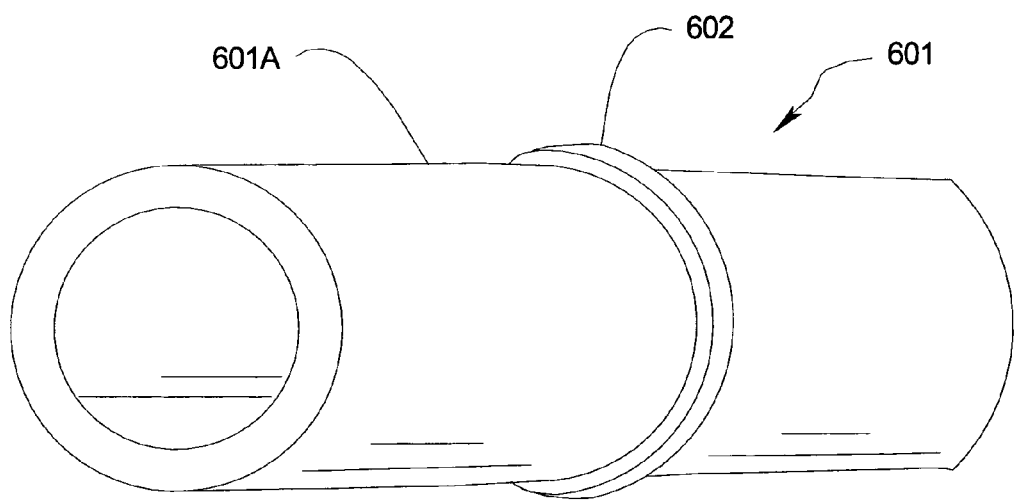
FIG. 6 is a perspective drawing of a hose having a degradation sensor band attached to the hose.

FIG. 6 is a perspective drawing of a polymeric product such as hose 601 having a sensor band 602 shrunk on an outside surface 601A of hose 601. Sensor 602 is a conductive composite having a matrix of a selected polymer having similar degradation characteristics as product or hose 601 material. In the preferred embodiments, the selected material comprises at least one of the polymeric components of hose 601 material. In a preferred embodiment, the selected polymer is an elastomer allowing a cold-shrink fit over outer surface 601A of hose 601. In other embodiments, sensor band 602 comprises a heat-shrink polymeric component, allowing heat shrinking of band 602 on hose 601. The conductive filler may be carbon black, a metallic powder, or a metallic oxide. A degradation control agent as discussed later may be added to sensor band 602.

Figure 7:
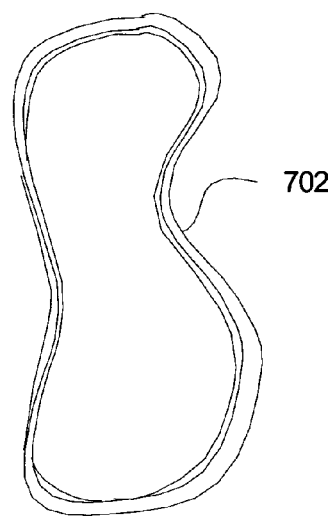
FIG. 7 is a perspective drawing of a degradation sensor formed as an elastic or shrinkable band for later attachment to a rubber product.

FIG. 7 is a perspective drawing of a sensor band 702, similar to that of sensor band 602 of FIG. 6 before installation on a product. Sensor band 702 is a conductive composite comprising a matrix of a polymeric material selected to have degradation characteristics similar to a product the band will be installed on and a conductive filler as described previously. Sensor band 702 may be an elastomer capable of expanding and cold-shrunk onto the product, or it may comprise a heat-shrinkable polymer for heat shrinking on the product. Sensor band 702 may comprise a degradation control agent as discussed later.

Figure 8:
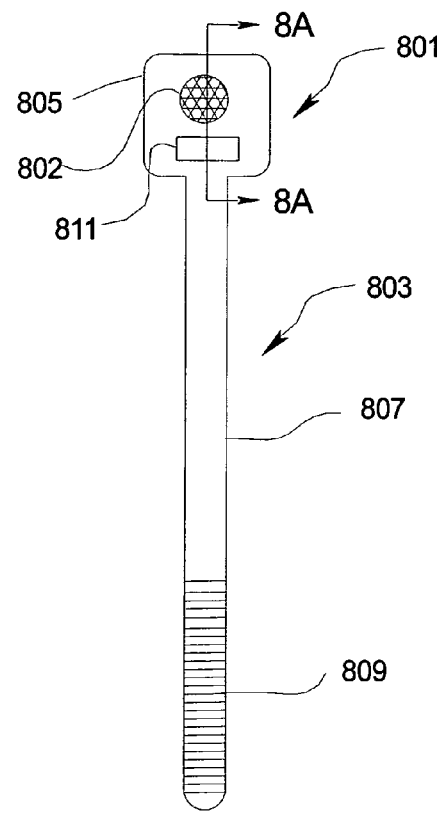
FIG. 8 is a mechanical fastener in the form of a tie wrap having a conductive composite degradation sensor attached to a head portion of the fastener.
Figure 8A:
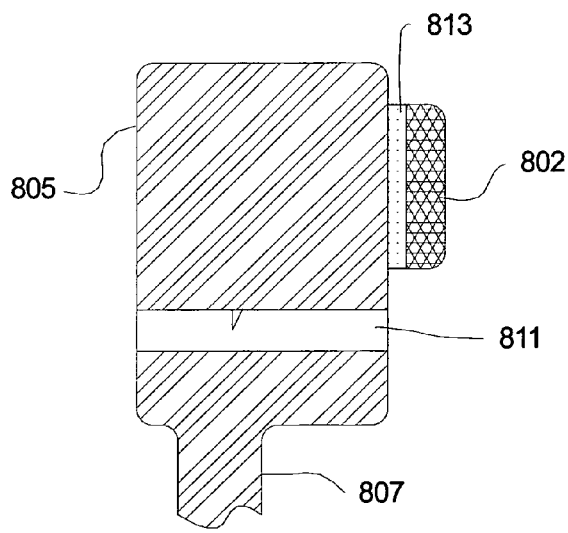
FIG. 8A is a cross section of the head portion of the fastener taken along lines 8A-8A of FIG. 8.

FIG. 8 is a front elevation drawing of a degradation sensing mechanical fastener 801 made by attaching a degradation sensor 802 to a wire-wrap type fastener portion 803. Fastener portion 803 is made of a strong, flexible material and comprises a head portion 805, and a strip portion 807. Strip portion 807 comprises a grooved end 809 securable in a securing aperture 811 as known in the art. FIG. 8A is a cross section of head portion 804 taken along lines 8A-8A of FIG. 8.

Sensor 802 is a conductive composite comprising a matrix of a polymeric material selected to have degradation characteristics similar to a product the fastener will be installed on and a conductive filler as described previously. In the preferred embodiments, sensor 802 is fabricated separately and may take the form of a disc such as a die-cut disc cut from a sheet of the sensor material cast, milled or extruded. In other embodiments, sensor 802 may be other shapes made by molding, extrusion, casting or milling. Sensor 802 may comprise a degradation control agent as discussed later.

As best seen in FIG. 8A, degradation sensor 802 is attached to head portion 805 by bond portion 813. In the preferred embodiments, bond portion 813 is an adhesive. In other embodiments, bond portion 813 is an adhesive tape. In still other embodiments, bond portion 813 is a mold bond between sensor 802 and head portion 805.

Other types of mechanical fasteners may be substituted for fastener portion 803 such as spring clips, bolted clamps, pin-type fasteners, and hook and loop fasteners.

Figure 9:
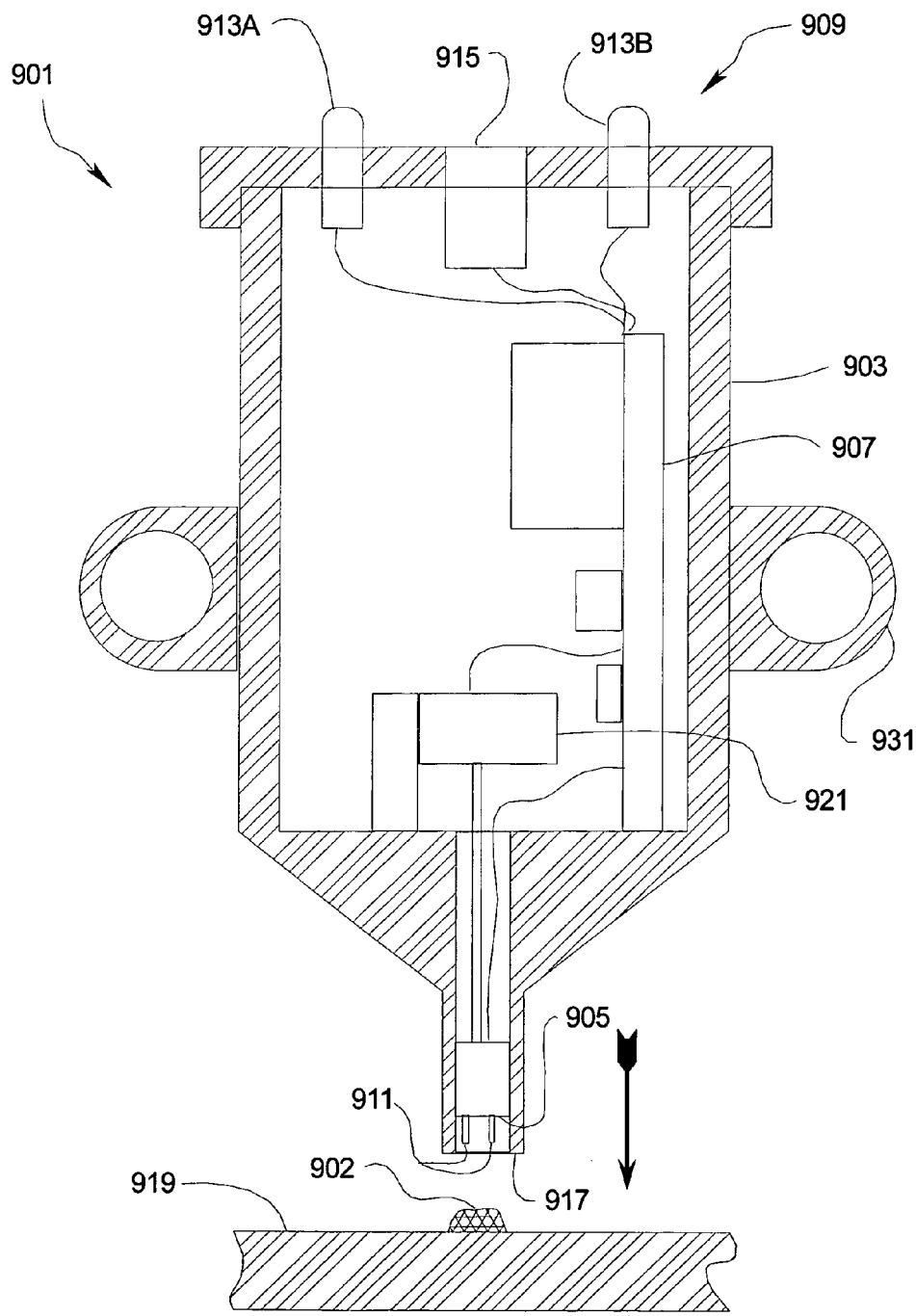
FIG. 9 is a cross section drawing of a contact reader for conductive composite degradation sensors having a recessed electrode assembly.

FIG. 9 is a cross section drawing of a contact-type sensor reader 901 for degradable products having conductive composite sensors as discussed. Reader 901 comprises a body portion 903, an electrode assembly 905, a processor 907 and an indicator portion 909. Electrode assembly 905 comprises two electrodes 911 connected to the processor 907. Processor 907 compares the resistance of sensor 902 as measured by electrodes 911 and provides a visual indication of the sensor status by LEDs 913A, 913B and an audio indication by audio transducer 915.

Figure 10:
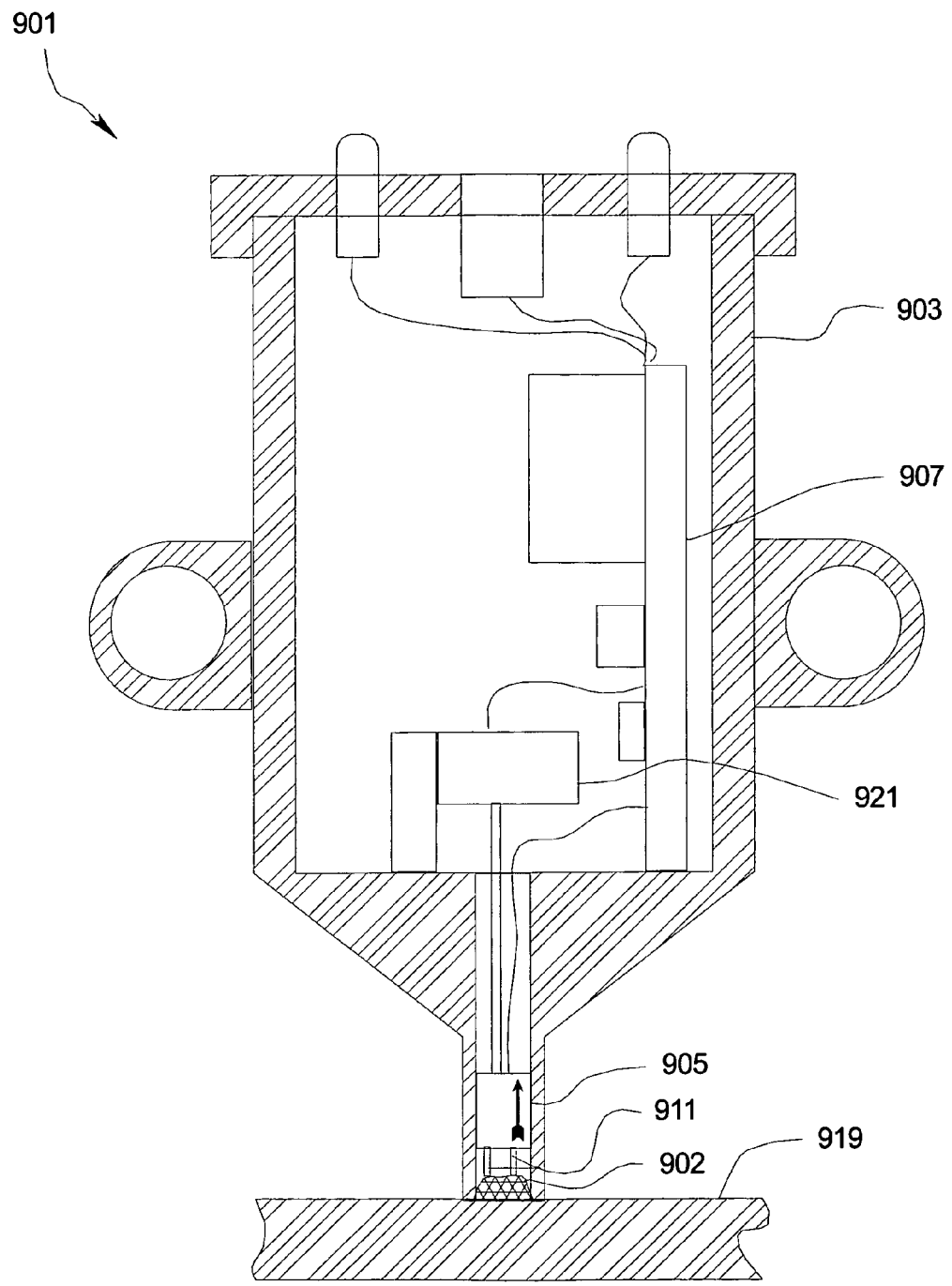
FIG. 10 is a cross section drawing of the contact reader for conductive composite degradation sensors of FIG. 9 with the electrode assembly inserted over a raised contact sensor and activating a microswitch of the reader.

In a preferred embodiment, electrode assembly 905 is recessed so that the bottom of electrodes 911 are recessed from the end of electrode shroud 917. This ensures that electrodes 911 contact only a sensor having a diameter smaller than electrode shroud 917 and raised above surface 919. In this preferred embodiment, electrode assembly 905 is attached to a micro switch 921, requiring depressing of electrode assembly 905 upward as shown in FIG. 10 in order to activate processor 907.

Figure 11:
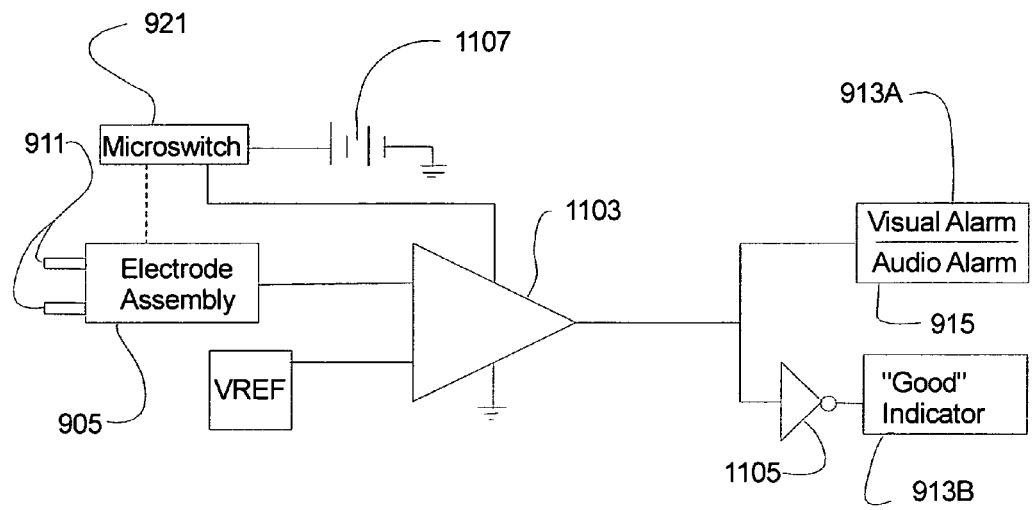
FIG. 11 is a block circuit diagram for the contact reader of FIGS. 9 and 10 having a comparator threshold function.
Figure 12:
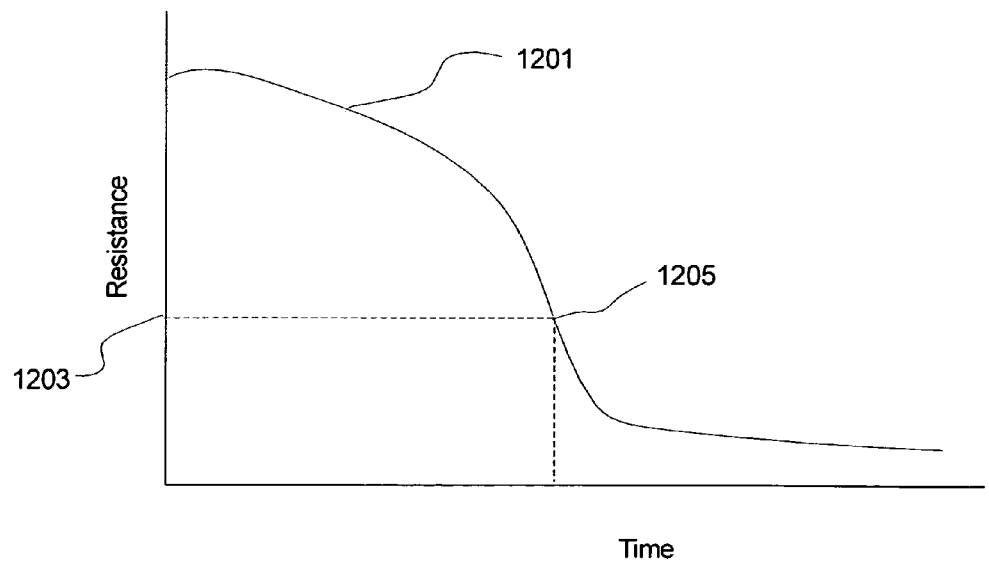
FIG. 12 is a resistance-time plot for a typical conductive composite degradation sensor for rubber products.

FIG. 11 is a schematic block diagram showing the circuitry of reader 901. A comparator 1103 compares a voltage developed across the resistance measured by electrodes 911 and compares it to a reference voltage provided by Vref. FIG. 12 is a resistance-time graph 1201 showing the typical sensor resistance response of a conductive composite degradation sensor with time. As the sensor attached to the product ages, the resistance of the sensor, as measured by electrodes 911 decreases due to shrinkage of the polymeric matrix component of the conductive composite sensor. A resistance 1203, corresponding to point 1205 on response curve 1201, is selected as a threshold value for a degraded product, based on correlation of accelerated aging a sensor and the monitored product.

Comparator 1103 provides a "failed" alarm output at visual alarm indicator 913A and audio alarm indicator 915 when the resistance of the sensor, as measured by electrodes 911 drops below the threshold value as determined by Vref. An inverting circuit 1105 provides a "good" output at indicator 913B when the resistance of the sensor is above threshold value 1202. Micro switch 921, mechanically connected to electrode assembly 905 and electrically connected between battery 1107 and comparator 1103 provides power to comparator 1103 only when electrode assembly 905 is depressed as shown in FIG. 10. In other embodiments, micro switch 921 is replaced with a manual switch. In still other embodiments, electrodes 911 extend to, or beyond the bottom of electrode shroud 917. Finger holes or grips 931 provide a means to better grip reader 901 and provide a "one hand" method to read a sensor such as sensor 902.

FIG. 13 is a perspective drawing of a drive belt such as V-belt 1301 incorporating a degradation sensor 1302. Sensor 1302 is shown in cross section drawing 13A taken along lines 13A-13A of FIG. 13. Sensor 1302 may be located on the top outer surface 1301A of belt 1301, or alternatively, it may be located on the inside surface 1301B as shown by sensor 1302B of FIG. 13. As better seen in FIG. 13A, sensor 1302 may be a separately formed conductive composite sensor disc attached to surface 1301A by an adhesive 1305 or other bonding methods as discussed earlier. Belt 1301 incorporates a reinforcement fabric 1307.

FIG. 13B shows an alternative embodiment with sensor 1302B mold bonded to belt material 1301C by utilization of a mold such as that shown in FIG. 2A. FIG. 13C shows yet another embodiment wherein sensor 1302C is a continuous layer of conductive composite material formed as the top surface of belt 1301D. Sensor layer 1302C may be separately formed and mold bonded to the belt during vulcanizing, or it may be separately formed and bonded to belt 1301D after vulcanizing.

Figures 14A, 14B:
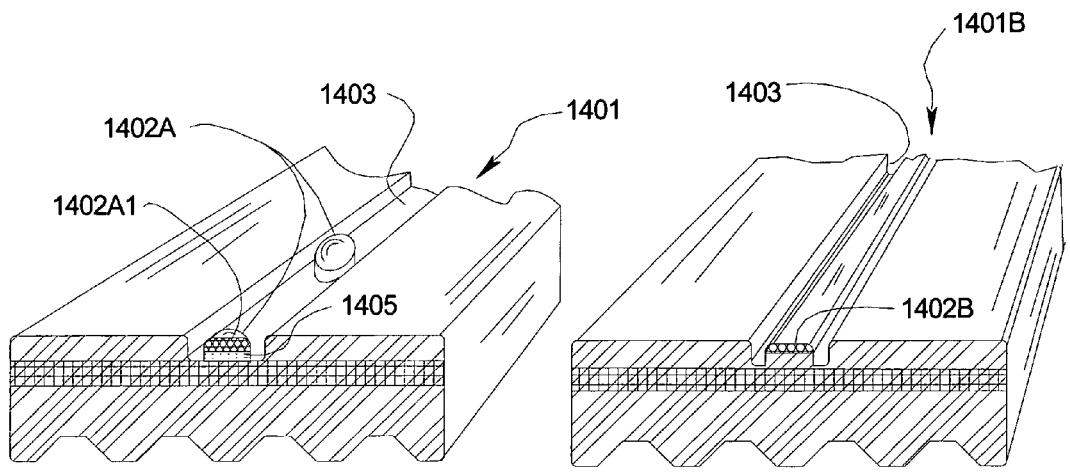
FIG. 14A is a perspective cross section drawing of a flat grooved belt having contact sensors disposed in a groove on the outside face of the belt.
FIG. 14B is a perspective cross section drawing of a flat grooved belt having a continuous contact sensor strip disposed in a groove on the outside face of the belt.

FIG. 14A is a perspective of a multi-grooved flat belt 1401, often utilized as a serpentine belt in drive applications. Sensors 1402A may be separately formed sensor discs 1402A1 and bonded to the top surface of groove 1403 by adhesive 1405, or they may be formed and attached by other methods described previously.

FIG. 14B shows another embodiment of belt 1401B having a continuous strip degradation sensor 1402B. Sensor strip 1402B may be separately formed and bonded to groove 1403 top surface by an adhesive, mold bonding, or other means.

Figures 15A, 15B:
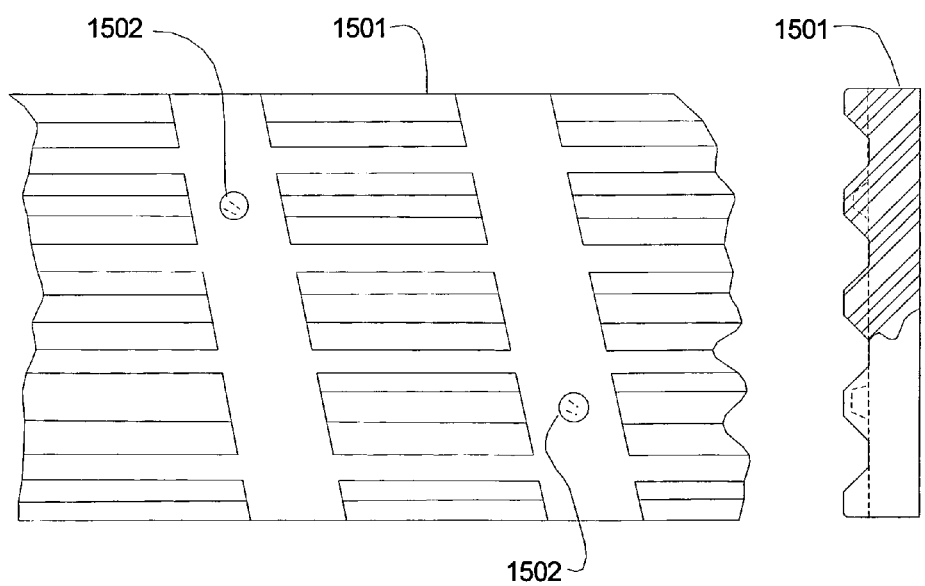
FIG. 15A is a view of the inside grooved surface of a flat drive belt showing contact degradation sensors disposed in spaces between ribb sections of the belt.
FIG. 15B is a partial cross section of the belt of FIG. 15A.

FIG. 15 is yet another embodiment of a flat belt 1501 having segmented grooves. FIG. 15A is a view of the bottom or inside surface of the belt and FIG. 15B is a partial cross section view Degradation sensors 1502 are attached to the inside surface of the belt between groove segments as shown in FIGS. 15A, 15B. Sensors 1502 may be attached by any of the methods discussed previously.

In all of the sensor applications disclosed, degradation sensors comprise a polymer matrix and a conductive filler. In the preferred embodiments, the polymer matrix comprises at least one polymeric component of the product being monitored. This ensures that the degradation mechanisms that affect the product also affect the sensor in a similar manner. Alternatively, a polymer matrix for the sensor may be selected which has a similar activation energy and/or time constant as the product polymer(s) when aged at multiple temperatures and subjected to Arrhenius evaluation as disclosed in prior referenced applications. Correlation between sensor resistance and product state may be determined by numerical techniques by accelerated aging of sensors and product material at multiple temperatures (or other environmental stress conditions) and correlating a measured degradation parameter (such as elongation at break, tensile strength or fatigue life) and sensor resistance.

In addition to selecting the polymeric matrix for the sensor to provide the desired correlation between sensor output and product state under multiple accelerated aging conditions, a control agent such as an anti-oxidant may be added to the polymer to adjust the degradation rate of the sensor. For example, many polymeric components such as tires, belts and hoses contain anti-oxidants to reduce the thermo-oxidative degradation effects. The selected sensor may utilize the same polymer and anti-oxidant as the matrix. The anti-oxidant level in the sensor matrix may be adjusted and act as the control agent to cause the sensor to respond faster or slower than the product to degradation stresses. For example, the anti-oxidant level of a sensor for tires, belts and hoses may be selected to be less than that of the polymeric component of the product, ensuring that the sensor ages faster than the product, giving a "safety margin" for warning of degradation of the product. Tests on EPDM materials suggest that addition of anti-oxidants slows the degradation rate of the polymer primarily by changes in the time constant in Arrhenius analysis, rather than changing the activation energy of the reaction.

Conductive fillers utilized in the sensors may include carbon black, carbon nanotubes, metallic, metallic oxide, and other conductive and semi-conductive particles. The conductive loading is selected to give reasonable sensitivity from degradation effects with a value low enough for ease of measurement by simple field equipment. In the preferred embodiments, the conductive filler loading is selected to give a standardized resistance at the sensor failure (product replacement value) for the product when untiring a standardized electrode configuration. In this manner, the same reader can test multiple products. Although threshold type readers disclosed are preferred to permit simple and objective repair/replacement of the product, correlation data of sensor resistance and degradation parameter data may be displayed as a continuous analog output, such as percentage of life remaining.

The degradation sensors and readers disclosed are effective in sensing hardening or loss of elongation due to thermo-oxidative degradation. In some applications, such as drive belts, tires and other applications involving high cyclic strain and fatigue, it may be advantageous to detect premature failure in cases where high-cycle strain results in cracking of polymeric belt material(s) even when the material still retains reasonable elasticity. This is especially the case in tires that are under inflated, or in drive belts having high duty cycles or high loads.

A combination fatigue and chemical degradation sensor may be used in these applications in which cracking of the sensor due to high-cycle fatigue increases the resistance of the sensor to a value much higher than the unaged value. A window type comparator may be used to discriminate between a failed sensor due to low resistance (severe chemical degradation) or very high resistance (due to a cracked sensor).

In the preferred embodiments, the combination sensor or multi-function sensor utilizes a polymeric component, control agent such as anti-oxidant level, or plasticizer level, or other means to ensure the fatigue life of the sensor is less than the fatigue life of the product material, so that the sensor will crack in a degraded state prior to the product and give adequate warning of impending failure of the product. In other embodiments, the physical location of the sensor is selected to ensure the sensor cracks before the product material of interest.

Figure 16:
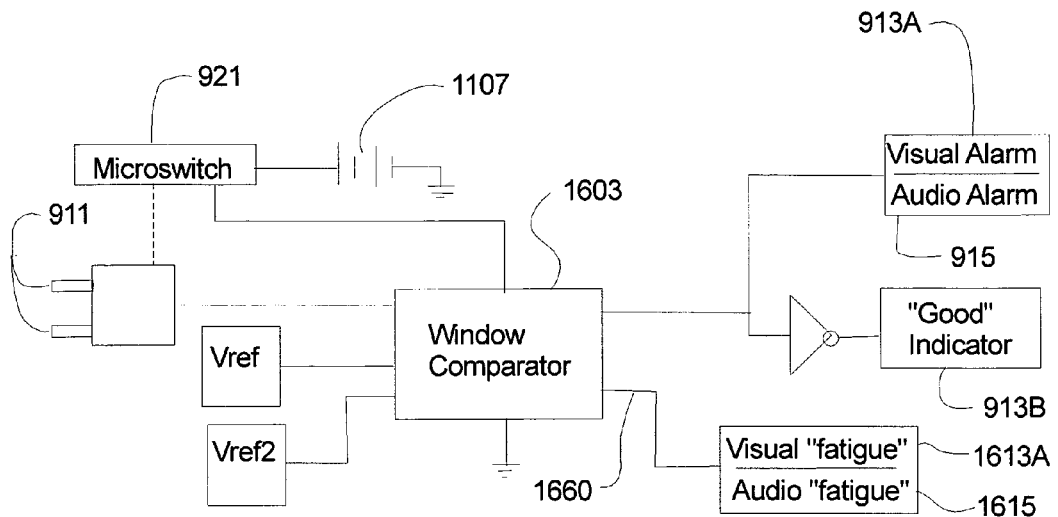
FIG. 16 is a block schematic diagram of a contact sensor reader having a window comparator for sensing both chemical degradation and cracking of a sensor.
Figure 17:
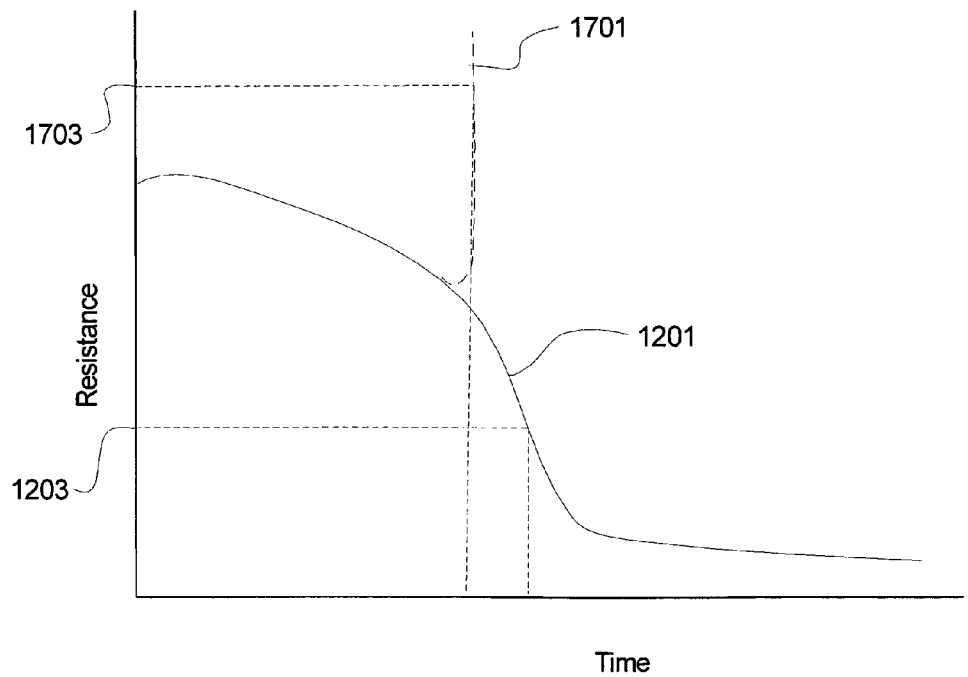
FIG. 17 is a resistance-time graph of a multi-function sensor approach for detecting both chemical degradation of a rubber product and fatigue failure of a high cycle product.

FIG. 16 shows a block diagram of a window comparator circuit for a multi-function sensor reader and FIG. 17 is a resistance-time curve for a multi-function sensor under chemical and fatigue stresses.

The block diagram of FIG. 16 is similar to that of FIG. 11, except that a window comparator 1603 is utilized instead of comparator 1103, and a second output for a second warning indicator (1613A visual, 1615 audio) is utilized to indicate a fatigue failure of the sensor. Vref2 input to window comparator 1603 provides output 1660 to fatigue alarm indicators 1613A and 1615 when the resistance of the sensor as measured at electrodes 911 is greater than value 1703 as indicated by cracked sensor curve 1701 curve in FIG. 17. Resistance value 1703 is greater than the normal chemical degradation value of the sensor at the beginning of life and represents an open or crack in the sensor due to fatigue. Fatigue failure occurs at a time shorter than that of the chemical degradation curve 1203.

Figure 18:
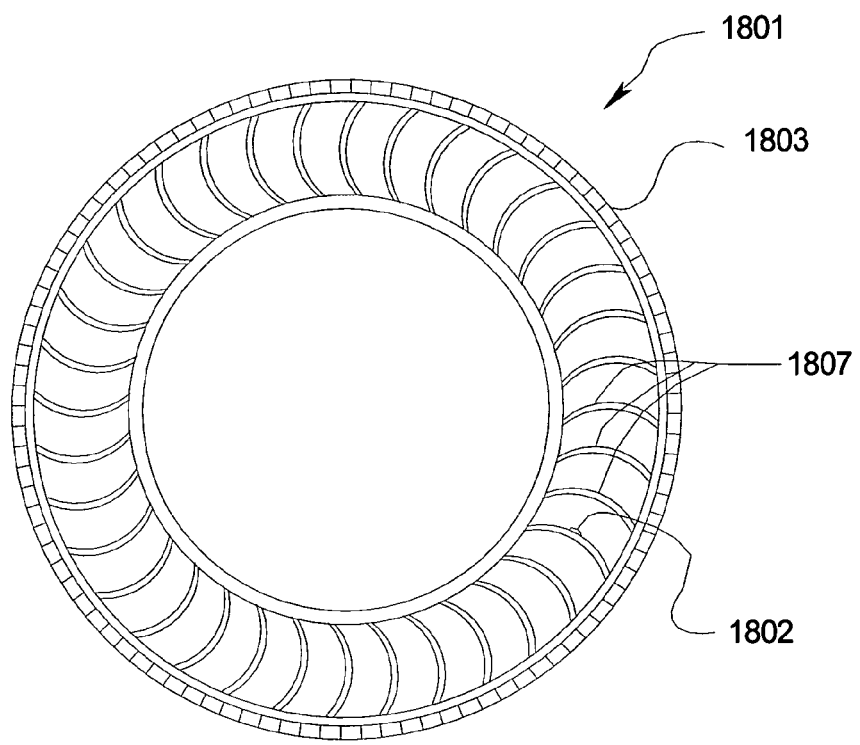
FIG. 18 is a side elevation drawing of a tire having polymeric spokes and a conductive composite degradation sensor for providing warning of both chemical degradation and fatigue failure of the spokes.
Figure 18A:
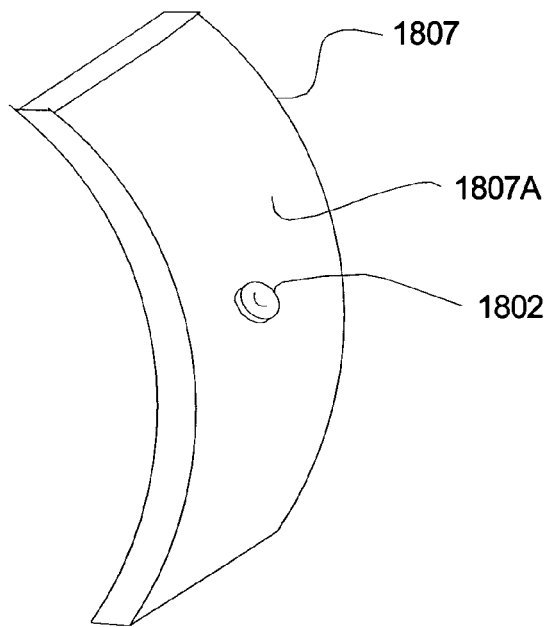
FIG. 18A is a detail perspective drawing of a spoke of the tire of FIG. 18 having a conductive composite sensor attached to a convex surface of the spoke.

FIG. 18 is a side elevation drawing of a composite tire 1801 having a rubber tread portion 1803, an inner rim portion 1805 and a plurality of polymeric spokes 1807. A degradation sensor 1802, attached to spoke 1807 shown in FIG. 18A, provides chemical degradation and fatigue sensing similar to the previous embodiments. Sensor 1802 is a conductive composite, and in the preferred embodiments comprises a polymeric component of spoke 1807 in the matrix of the sensor. In a preferred embodiments, sensor 1802 is disposed on a convex surface 1807A of spoke 1807 where strain is maximized during use. Any of the methods disclosed may be used to form or attach sensor 1802 to spoke 1807, including bonding the sensor after fabrication of the spoke, co-forming with the spoke, or other attachment means.

FIG. 19 shows a passive RFID tag or smart label 1901 comprising a passive RFID chip 1903, antenna 1905, conductive composite sensor 1902 and circuit board 1907. In the preferred embodiments, RFID chip 1903 comprises a sensor input such as that made by Microchip Inc. (MCRF-202) providing inversion of data code upon data input of a sensor. In the preferred embodiments, RFID tag 1901 provides the inversion upon a preselected threshold resistance of sensor 1901 as discussed previously, and as disclosed in the prior referenced applications. In a preferred embodiment, RFID tag 1901 is encapsulated in an insulative coating or molded cover 1909 to form an encapsulated RFID tag for mechanical protection during handling and installation in a product.

FIG. 20 is an elevation drawing of RFID tag 1901 disposed in an industrial rubber product such as tire 2001. In the preferred embodiments, the tag is attached to the inside surface 2001A of tire 2001 on a sidewall as best seen in encapsulated tag 1901A and molded tag 1901 FIG. 20A. Tag 1901A may be bonded by an adhesive 2007 or other bonding methods known in the art.

Use of RFID tag 1901 eliminates electrical contact of a reader with sensor 1902 and allows wireless communication of tire 2001 identification data and degradation condition of the tire with reader 2003 of FIG. 20. In the preferred embodiments, sensor 1902 comprises a polymeric component of tire 2001, and in the more preferred embodiments, sensor 1902 comprises a limiting life polymeric component of tire 2001 as a matrix component of the sensor.

Figure 21:
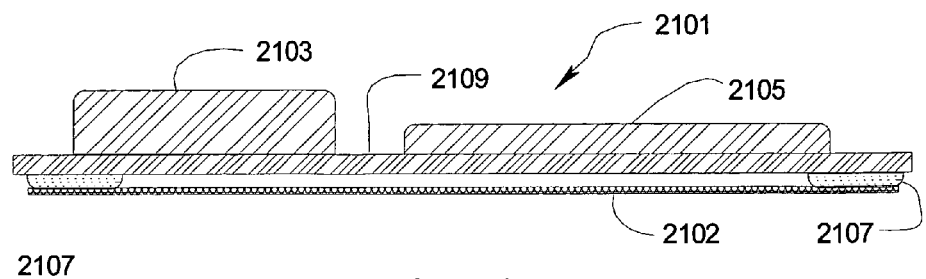
FIG. 21 is a cross section drawing of another embodiment of a smart tag with integral sensor having chemical and fatigue sensing capability.

FIG. 21 is a cross section drawing of another embodiment of a smart tag 2101 with chemical and fatigue sensing capability. Multi-function sensor 2102 is a conductive composite sensor mounted on a back side of tag 2101 and connected to RFID 2103 by conductive adhesive pads 2107. In the preferred embodiments, circuit board 2109 is a flexible board and antenna 2105 provides communications and power means to RFID 2103. Placing sensor 2102 on an outer surface of the tag and extending over a substantial length of the tag facilitates integration of the tag into a product for sensing both chemical degradation and fatigue as discussed earlier.

Figure 22:
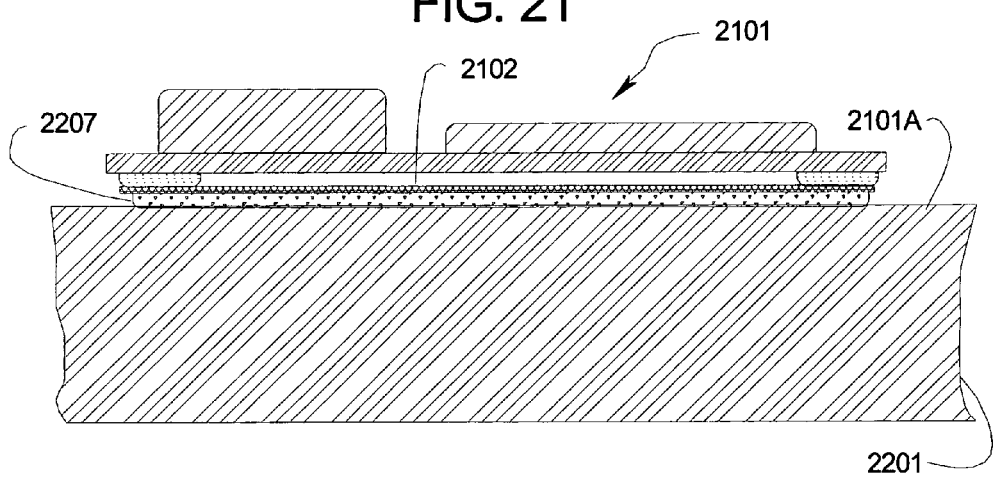
FIG. 22 is a cross section drawing showing a combination RFID tag and sensor attached to an outside surface of a degradable product by a bonding agent.

FIG. 22 is a cross section drawing showing tag 2102 attached to an outside surface 2101A of product 2201 by a bonding agent 2207. Bonding agent 2207 may be an adhesive or other bonding means as described in previous embodiments.

Figure 23:
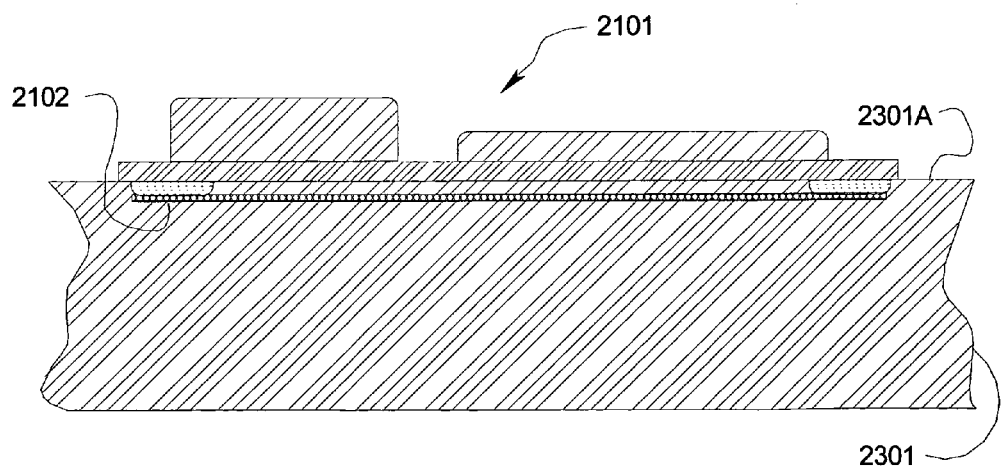
FIG. 23 is a cross section of yet another embodiment showing mold bonding of a combination RFID tag/sensor to a product.

FIG. 23 is another embodiment showing mold bonding of tag 2101 to a product 2301. Tag 2101 may be place in a mold with sensor 2102 extending into the mold cavity to allow sensor 2102 to be embedded into product 2301. A cavity well, similar to that shown in FIG. 2A may be provided to control the depth of tag 2101 above, level with, or below surface 2301A.

Attaching or embedding sensor 2102 to the product allows sensor 2102 to provide an output corresponding to chemical degradation or fatigue as discussed in previous embodiments. Sensor 2102 may be selected to have a similar activation energy to allow chemical degradation response similar to, or faster than, the product material degradation, and possessing a fatigue life less than the product material. Using the same polymer as the product material and utilizing less anti-oxidant will result in faster degradation of the sensor and faster failure when strained for the same environmental aging of the product. Fatigue life selection may also be adjusted by modifying the matrix materials of the sensor or adjustment of other control agents such as plasticizers.

Although the description above contains many specifications, these should not be construed as limiting the scope of the invention but merely providing illustrations of some of the presently preferred embodiments of this invention. Thus the scope of the invention should be determined by the appended claims and their legal equivalents, rather than by the examples given.

I claim:

1. A rubber product with integral environmental degradation sensor, said sensor comprising:
   a polymeric matrix comprising an activation energy of degradation similar to at least one polymeric component of the rubber product;
   a conductive filler; and
   a means for communicating sensor resistance to a reader; wherein the sensor resistance changes with time as a result of an environmental stress on said rubber product.

2. The rubber product of claim 1 wherein said degradation sensor comprises a control agent for adjusting the degradation rate of said sensor.

3. The rubber product of claim 2 wherein said control agent is an anti-oxidant.

4. The rubber product of claim 3 wherein said anti-oxidant is adjusted to a level less than said at least one polymeric component of said rubber product whereby said degradation sensor degrades at a rate faster than said product.

5. The rubber product of claim 1 wherein said polymeric matrix is a polymeric component of said product.

6. The rubber product of claim 1 wherein said communication means is a surface of said sensor disposed on an outside surface of said rubber product whereby said sensor resistance may be read by a contact resistance reader comprising contact electrodes.

7. The rubber product of claim 6 wherein said sensor is a disc attached to said product by an adhesive.

8. The rubber product of claim 6 wherein said sensor is a disc molded to said product.

9. The rubber product of claim 6 wherein said sensor is applied to the product as a hot melt compound.

10. The rubber product of claim 1 wherein said sensor is attached to said product by a mechanical fastener.

11. The rubber product of claim 10 wherein said sensor is attached to said mechanical fastener.

12. The rubber product of claim 10 wherein said mechanical fastener is a tie wrap.

13. The rubber product of claim 1 wherein said communication means comprises said sensor electrically attached to a passive radio frequency identification device disposed on said product.

14. The rubber product of claim 1 wherein said product is a tire.

15. The rubber product of claim 14 wherein said sensor is electrically attached to a passive radio frequency identification device disposed on said tire.

16. The rubber product of claim 1 wherein said product is a hose.

17. The rubber product of claim 1 wherein said product is a belt.

18. The rubber product of claim 1 wherein said environmental stress is temperature.

19. A degradation sensor assembly for use with degradable rubber products comprising:
    a mechanical fastener attachable to said rubber product; and
    a degradation sensor attached to said mechanical fastener, said sensor comprising a polymeric matrix having an activation energy of degradation similar to an activation energy of degradation of at least one polymeric component of said rubber product and a conductive filler, and
    a communications means for communicating sensor resistance to a reader;
    wherein the sensor resistance changes with time under an environmental stress of the rubber product and wherein said resistance is correlatable with a resistance of a previously environmentally degraded rubber product.

20. The degradation sensor assembly of claim 19 wherein said mechanical fastener is a tie wrap comprising a strip portion and a head portion comprising a strip portion aperture and wherein said degradation sensor is attached to said head portion.

\* \* \* \* \*